United States Patent [19]

Moreaux

[11] 4,057,998
[45] Nov. 15, 1977

[54] CHROMATOGRAPH, MORE PARTICULARLY FOR GAS PHASE CHROMATOGRAPHY

[75] Inventor: Claude Moreaux, Livry-Gargan, France

[73] Assignee: Societe Anonyme Intersmat, Pavillons-sous-Bois, France

[21] Appl. No.: 702,875

[22] Filed: July 6, 1976

[30] Foreign Application Priority Data

July 9, 1975 France .............................. 75.21528

[51] Int. Cl.$^2$ .......................................... G01N 31/08
[52] U.S. Cl. .................................................. 73/23.1
[58] Field of Search ........................ 73/23.1; 219/394

[56] References Cited

U.S. PATENT DOCUMENTS

| 3,053,077 | 9/1962 | Tracht .................................. 73/23.1 |
| 3,686,930 | 8/1972 | Kniebes et al. ....................... 73/23.1 |

*Primary Examiner*—Charles A. Ruehl
*Attorney, Agent, or Firm*—Young & Thompson

[57] ABSTRACT

This chromatograph comprises a modular enclosed space having compartments, with temperature controlling means arranged in said compartments, such as an electrical resistance and a blower, for providing a uniform temperature. Removable function modules are selectively insertable in said compartments. Said function modules may comprise for instance injection modules, column modules, detection modules, valve modules, and modules for physical or chemical conversion. Means are provided in said compartments for receiving and locking said function modules. A matrix which can comprise external coupling positions and interconnections between said positions is provided for interconnecting the function modules according to the analysis problem to be solved. If desired, the interconnections of the matrix may be selectively changed. Such a chromatograph is adaptable, by selecting suitable function modules and interconnections, for solving any analytical problem in gas phase chromatography.

11 Claims, 9 Drawing Figures

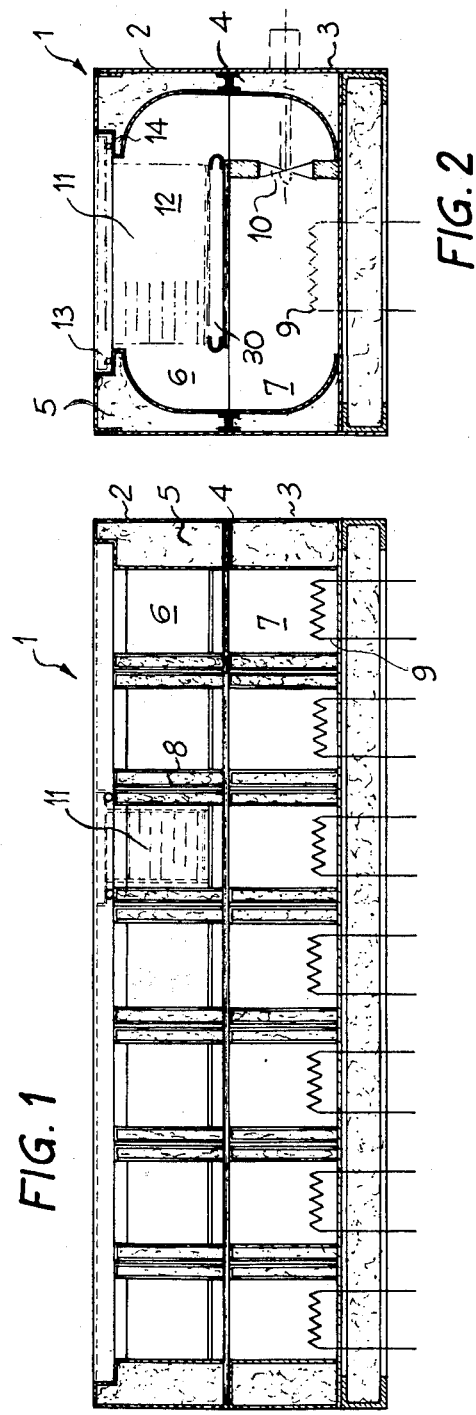
FIG. 1
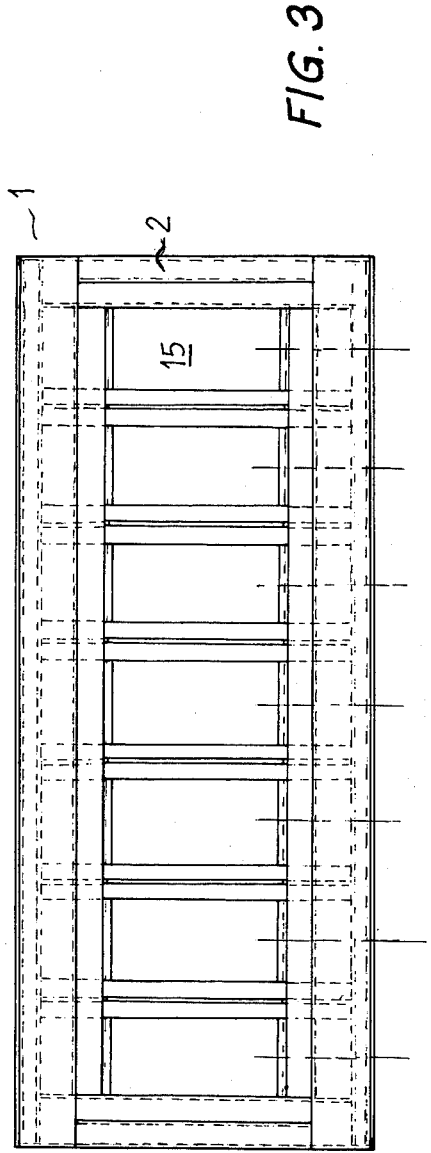
FIG. 2
FIG. 3

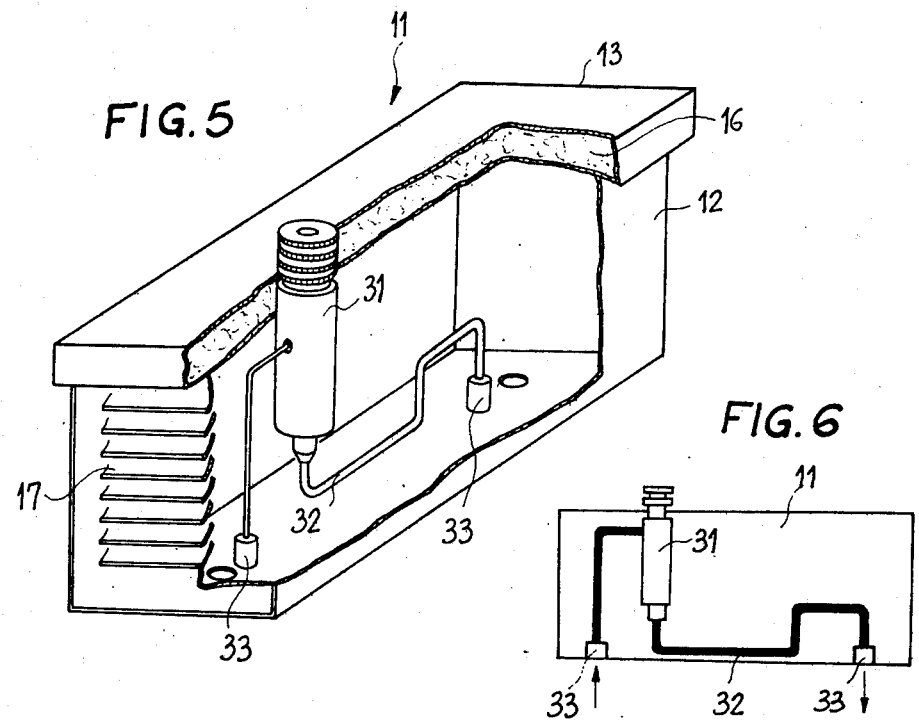
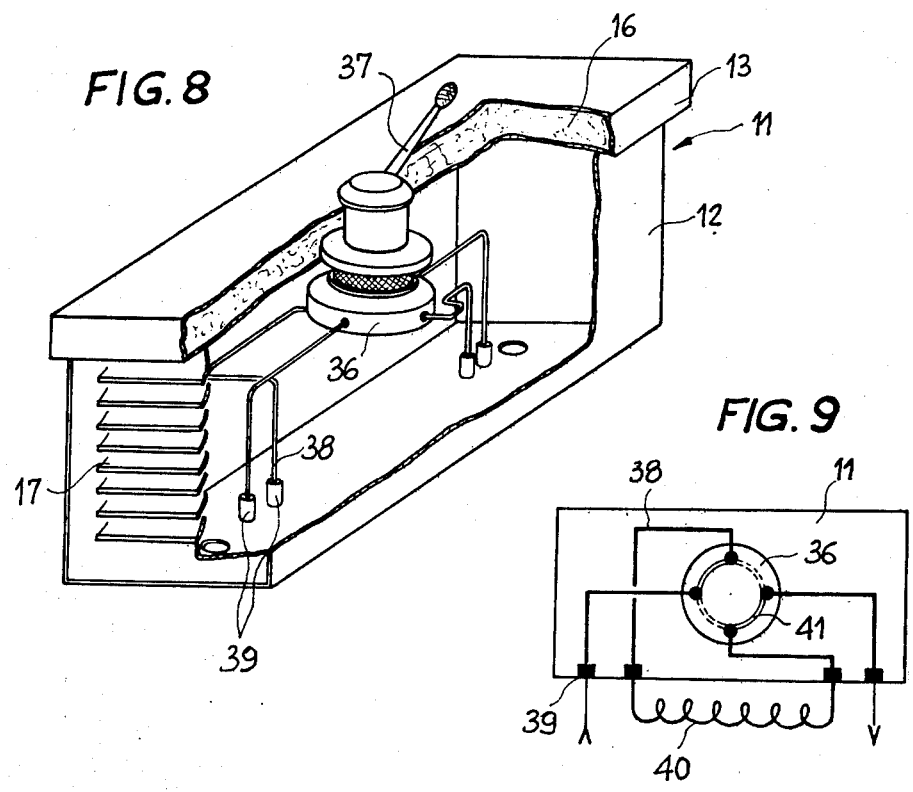

CHROMATOGRAPH, MORE PARTICULARLY FOR GAS PHASE CHROMATOGRAPHY

This invention relates to chromatography, more particularly, to gas phase chromatography.

Gas phase chromatography is a technique for separating mixtures, often complex, of volatile substances, or substances which can be rendered volatile, for example by modification or conversion, permitting not only their qualitative analysis, but also a quantitative measurement of the constituents of these mixtures and a production of the latter in a form sufficiently pure for their utilization in particular applications or for their analysis by other methods of identification.

A chromatograph intended for this technique generally comprises a source of carrier gas, a system of regulation for the flow rate of this gas, a device for injecting the sample to be analysed into this stream of carrier gas, a separation column traversed by the carrier gas and the sample to be analysed, and a system of detection placed downstream from the column and associated with a recorder for the readings.

At present the devices are all structured according to this well defined combination. Although the three principal elements of the chromatograph proper, constituted by the injector, the furnace, i.e. the enclosed space surrounding the separation column, and the detector, may well be separately stabilized in temperature, the furnace is generally the only point where the temperature may be programmed.

It has already been proposed to mount two separation columns in the furnace and then direct the carrier gas along with the injected sample towards one or the other of these columns by means of valves which are generally placed either in the furnace in order to permit certain analytical operations, or to provide one valve to obtain an inversion of the circulation in the column.

It has also been proposed, in French Pat. No. 71.42407, filed Nov. 26, 1971, to provide a chromatograph comprising removable modules each having an injection chamber, a separation column and a detection unit, and simultaneously to use several such modules for simultaneously resolving several analytical problems, whereby the separation columns of the modules can be set at different temperatures during the chromatographic analysis.

However, each of these existing chromatographs is a device of predetermined structure and adapted to one type of analysis, and so is unable sometimes without complex and costly artifices to solve the problems of analysis arising in other particular techniques.

The aim of the invention is to solve this problem and to create a chromatograph, the arrangement of which enables, on the basis of a single device, a functional adaptation to be made to the particular problem of analysis under consideration, i.e. the device can be appropriated in fact to the analytic solution selected by the chromatographist.

To this end of the invention is to provide a chromatograph, more particularly for gas phase chromatography, comprising a modular enclosed space with compartments, means for temperature regulation within each compartment, removable function modules selectively insertable into the compartments of this modular enclosed space, the nature of each module being adapted to the function which is assigned thereto in the chromatographical analysis, means provided in the compartments for reception of the function modules, and means for selective inter-connection of the function modules according to the analytical problem being solved.

The enclosed space can be formed by a housing which delimits a definite number of compartments or cells to form a unitary structural assembly, and the compartments are thermally insulated in relation to each other as well as the external medium.

Each compartment internally accomodates temperature control elements, particularly heating elements such as electrical resistances, and these elements are combined preferably with at least one blower or an equivalent device, enabling a uniform controlled temperature to be obtained throughout the compartment under consideration.

Outside the enclosed space, these temperature control elements are connected to a system of regulation and control which can be a programming system or a calculator of some kind, and so able in each compartment to achieve an isothermic temperature or temperature programming as required.

The function modules used in employing the invention can be of very different types. Provision can notably be made for injection modules, valve modules, column modules, detection modules and hybrid modules containing, for example, a column and one or several valves, or equally even a control detector.

These modules could be adapted with a view to perform physical and/or chemical conversions which are intended to intervene in the operation of analysis, i.e. operations which are involved in the analysis without being essentially chromatographic functions.

The means of reception of the modules within the compartments are so arranged as to permit positioning of the module and its securing. It is obvious that many solutions will be apparent to those skilled in this field, the means provided being automatic or manually controlled.

Connection of the modules in accordance with the analytical problem to be solved can be ensured by means of a removable or interchangeable matrix which preferably is preconnected in accordance with the problem to be solved. In that case, connecting or fastening elements provided on the function modules and projecting in relation to the modules will cooperate with complementary parts of the matrix. The function modules and the matrix can then be joined together by automatic connections.

It is also possible, however, simply to provide, for example, a perforated matrix for insertion of the connecting elements of the function modules, and to establish the connections required by means of screwed unions, for example, of conventional type.

As indicated above, the temperature control elements of the compartments are connected to an external system of regulation and control. More generally, the operational parameters which must be taken into account for the function modules can be controlled by a programmer unit which is itself programmed in advance according to the problem to be analysed and having a capacity adapted to the number of compartments and so to the number of modules, or the apparatus can equally well be connected to an electronic computer for controlling these parameters. In particular, such a computer can control the isothermic or programmed temperatures in the various compartments, besides control of the gas flow rates and of the states of the injection or commutation valves.

It will be clear that the invention thus permits providing a chromatograph of great flexibility in use and in which, for example, several columns can be provided to inter-relate their separation effects in view of the analytical problem to be solved, and each column or, more generally, each part of the chromatograph can be controlled in temperature or by reference to some other parameter. Thus the analyst, from consideration of the problem posed, can define at will his method of operation and then adapt the apparatus with a view to applying the method without preoccupying himself with the practical requirements which have been imposed hitherto by the structural rigidity of the existing devices.

The following description in reference to the attached drawings, given non-restrictively, will enable the invention to be better understood.

FIG. 1 is a longitudinal sectional view of the housing of a chromatograph according to the invention.

FIG. 2 is a corresponding cross-sectional view of a compartment with function module.

FIG. 3 is a schematic representation of the device in plan view.

FIG. 5 is a perspective view, partially cut away, showing an injector-type function module usable according to the invention.

FIG. 6 is a schematic representation of this module.

FIG. 8 shows a perspective, partially cut away view of another function module which forms an "inverse circulation valve".

FIG. 9 is a schematic representation of the latter function module.

Figure 4:
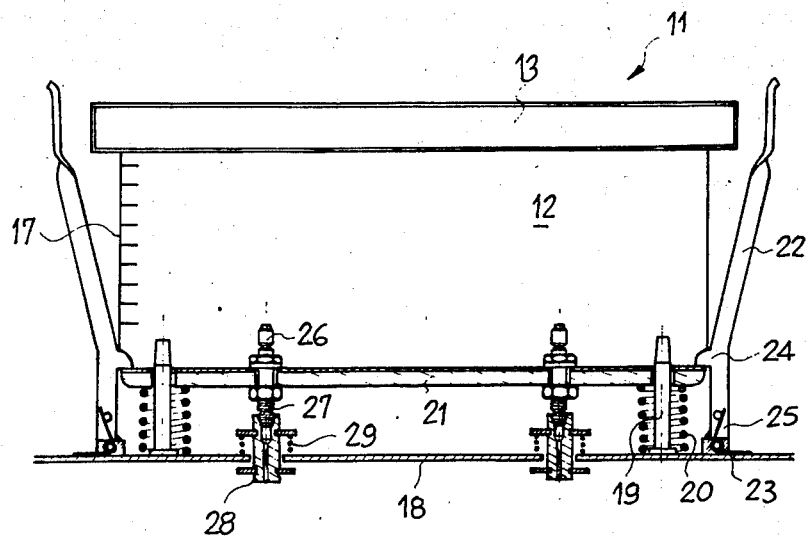
FIG. 4 is a partial view in front elevation with a partial section showing the means of positioning, securing and connecting a function module in the case of the embodiment illustrated.

If reference is first made to FIGS. 1 and 3, it will be seen that the chromatograph of the invention comprises an enclosed space in the form of a housing which is designated generally by numeral 1 and is in the present case provided with an upper part 2 and a lower part 3 which can be joined together by means of a hinge (not shown), and between which tightness is ensured by the joint indicated schematically as 4. Each part 2 and 3 is insulated in relation to the exterior, as shown by 5, and subdivided into compartments or cells so as to obtain compartments 6 in the upper part of the housing and compartments 7 in its lower part. The compartments 6 and 7 are also insulated thermally in relation to one another, as indicated by 8 in FIG. 1.

According to this embodiment, provision is made for seven compartments 6, 7, but it will be clear that this number can be varied according to the needs and capability of the apparatus considered.

Each lower compartment of the housing accommodates means for temperature regulation, represented here as an electrical resistance 9, but also able to be of a different type. Outside the apparatus, these resistances 9 are connected to a system for programming or regulation to which reference will be made later.

According to this embodiment, provision is also made for each lower compartment 7 to contain a blower 10 which is operated under external control and ensures uniformity of the temperature required within each compartment. The atmosphere, the temperature of which is regulated by means of the resistance 9, is thus made uniform within the double compartment 6, 7.

A schematically shown function module 11 is fitted in one of the compartments 6, 7 of the housing.

Figure 7:
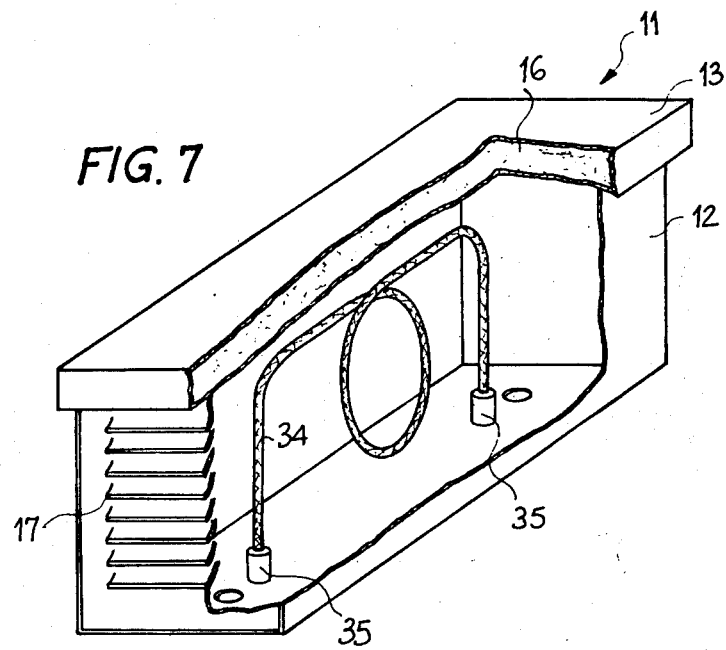
FIG. 7 is a perspective, partially cut away view similar to FIG. 5, but relating to a "column" module.

A function module of this type generally comprises, as will be still more clear in FIGS. 4, 5, 7 and 8, a body 12 which enters the upper compartment 6 of the housing and an upper cover 13 which projects beyond the body and rests by this projecting part on the shoulder 14 provided in the upper part of the housing (FIG. 3) for insertion of the function modules with an interposed seal. As shown in FIGS. 5, 7 and 8, the cover 13 of the function modules 12 is hollow, and contains thermal insulation 16 to complete the thermal insulation in relation to the exterior.

From the drawings, it will further be seen that the modules are constituted by similar blocks or bodies within which the various operational elements are simply placed so as to make the modules interchangeable. It will also be seen in the drawings that the bodies 12 of the function modules 11 have a lateral louvre 17 which permits circulation, within the function modules, of the atmosphere agitated by the blower 10, so that the function elements of the module are brought to the desired temperature.

In FIG. 4, the means for positioning, securing and connecting the function module are shown in more detail. Here the support plate 18 mounts guiding pins 19 surrounded by helical springs 20 and on which the base 21 of the module engages by appropriate orifices to position the module 11 within the associated compartment. The support plate 18 further serves to mount the locking levers 22 which are free to pivot about axis 23 in their seatings and are provided with a lip 24 which, in the locking position illustrated in FIG. 4, so engages the base 21 of the module from above that the module is reliably secured. The levers 22 are urged towards their working position by torsion springs 25. They can be removed from the module by applying counteracting force when the module is to be released. On release, the helical springs 20 act in the manner of ejection springs, which facilitates withdrawal of the module from the housing of the apparatus.

It will further be seen from FIG. 4 that the base of each module also has the fixed fastening components 26 which by the cone 27 associated with a packing ring can engage the equally tapered part of a moving fastening component or connector 28 under the action of the spring 29. This arrangement, used in the embodiment under consideration, permits automatic connection of the module to the moving components 28 which are mounted on the plate support 18.

In the present case this plate support 18 forms part of the matrix shown schematically as 30 in FIG. 2 and which contains or carries the various connections which have to be made between the function modules inserted into the housing in order to solve the analytical problem in question. One such matrix is fitted between the two parts 2 and 3 of the housing of the apparatus. In this case it is selected according to the particular problem to be solved, and then a certain number of matrices can be arranged in accordance with pre-determined connections between the function modules.

However, it is equally possible to have a matrix simply comprising a plate support and connections such as the moving connections 28 in FIG. 4 between which the desired couplings are made at will, having regard to the analytical problem still to be solved. A connection or coupling matrix can therefore be prepared according to the problem considered and the type of function modules employed, then this preconnected matrix can be mounted in the housing of the apparatus in order to place the modules, the desired connections between the modules being effected automatically as indicated in FIG. 4.

Another solution further consists in providing a plate support or matrix which simply has orifices that are traversed by the fixed components 26 of the function modules, which then have a greater length, the fixed connections exhibiting at their end connecting elements, for example, by screwing, of conventional type, in which case the desired connections or couplings are then made between the connectors of the function modules after they have been placed in position.

Reference will now be made to FIGS. 5 to 9 which show usable function modules.

In FIGS. 5 and 6 a function module serving as an injector is illustrated. As mentioned previously, this module includes a body 12 with a cover 13 and a louvre 17 which is provided in the body for circulation of the atmosphere of the compartment in which the function module is inserted. The injector proper, designated as 31, is interposed in a pipe 32 between the two unions 33. In FIG. 6 arrows schematically indicate the path of the carrier gas into which the injection should take place.

FIG. 7 shows a function module which forms a column and in the present case comprises a column 34 of appropriate type, mounted in the unions 35 which are provided in the base of the function module.

FIGS. 8 and 9 show a function module of the type forming a reverse circulation valve. In this case the body of the module, of the same type as previously, contains the valve body proper 36 which is controlled in the present case by a small handle 37 and is connected by the pipes 38 to the unions 39 in the base of the module. The role played by this valve-forming module is schematically illustrated in FIG. 9. A column is schematically indicated as 40, whilst the continuous lines 41 represent the parts establishing communication within the valve body. It will be seen that in the position represented in FIG. 9 the circulation within the column 40 is in a certain direction, whilst on inversion of the valve by a 90° displacement the circulation takes place in the reverse direction within this column 40, without modifying the general direction of circulation in the module.

The use of a chromatograph of the type described will be easily understood from the description and the drawings. It will be seen that by using a housing of the type represented in FIGS. 1 and 3 and comprising a number of compartments in which the temperature can be controlled as desired, it is possible, by the use of appropriate function modules and establishing the desired connections, either manually or automatically with the aid of a preprogrammed matrix, to adjust the apparatus to any analytical problem, as desired, by combining different functions to be performed and separately regulating the temperature for each of these functions. In the present case, the device can be termed a multi-furnace chromatograph, which permits complex analysis by the use of several columns and/or several valves and/or several detectors, with, eventually, other intermediate operations of a physical or chemical nature.

As indicated previously, the means 9 for temperature regulation associated with each of the compartments 6, 7 can be connected to a programming system such as an electronic computer which within each compartment provides a temperature which is either isothermic or varies according to a program. Moreover, the valves or other elements mounted in the function modules can also be controlled automatically by external means, e.g. from a computer. Such a control can, if desired, be ensured after a detection, so as to permit, during the analysis, cuts to be provided, or connections to be made at the desired time, as set for instance by the result of the detection.

In order better to show the capabilities of such an apparatus, its application will be described below by taking two examples.

EXAMPLE 1

The problem posed in this use is an analysis of hormonal steroids.

The problem having been posed, the analyst can for example select the following method of working:

For the analysis, begin with the injection of an ethereal solution of hormonal steroids, adjusting the injector to an average temperature of 100° C and effecting the injection at the top of a short column of glass beads, for instance, with a slow gas rate of flow on this column so as to eliminate the solvent, constituted by the ether, without degrading the steroids. Then evacuate the ether to a control column so as to follow the drying of the product. During this operation the analytic column is held at a raised temperature and at a nominal carrier gas flow rate equal for example to 20 ml/min. When drying is completed, as indicated by the control detector signal, the carrier gas is replaced by a stream of silylating gas also at 100° C, this stream of gas being maintained throughout the period necessary to achieve the reaction (5 min in the present case). Then continue drying again in nitrogen in order to complete elimination of the reagent and volatile by-products.

At the start of the operation, the commutation valves are set in such a position that the carrier gas, supplied at nominal flow rate, comes directly to the analytic column. After the said silylation operation, the injection of all the silylated steroids at the top of the analytic column is ensured by a rapid rise of temperature on the glass bead column to 250° C in several seconds for example. A temperature gradient of 4° to 6° C/min is then applied to this column so as to proceed with analysis of the silylated derivatives of the steroids.

At the start of this analysis the injector is restored to the initial conditions with a view to a further injection, without waiting for the end of the analysis.

It is self-evident that this sequence of operations can be pre-programmed by means of an electronic computer. The foregoing operation can be conducted with the apparatus which is the object of the invention using six modules, i.e.:

A module No. 1 comprising a four-way valve and two pressure drops, and serving to ensure the carrier gas flow rates desired at different places.

A module No. 2 comprising a four-way valve and a silylation reagent bubbler.

A module No. 3 comprising an injector and a pre-column.

A module No. 4 comprising a four-way valve, a small column and a control detector which can be a catharometer or of other type.

A module No. 5 comprising an analytic column (semi-capillary for example).

A module No. 6 comprising the detector.

Appropriate connections between the different modules by means of a matrix and the intervention of the computer enable the afore-mentioned different operations to be performed with the apparatus. No existing chromatograph is at present able to make such an analysis by such simple means.

EXAMPLE 2

In this case it is desired to analyse traces of matter with a re-injection of narrow cut. A complex mixture is then injected at the top of a selective column and the separation is followed on a control detector so as to evaluate with precision the moment at which the product can in trace amounts be derived on another column with a view to achieving a finer separation.

This problem is in itself simple and can be solved on a standard chromatograph. The apparatus of the invention enables however, in this case, the use of a second column at a different temperature to that of the first and which can even be programmed.

The problem can be solved by the apparatus described with five modules, namely,

A No. 1 module with a four-way valve.
A No. 2 module with an injector.
A No. 3 module with a four-way valve, one column and a control detector.
A No. 4 module with one column.
A No. 5 module with a detector.

In this case also the connections between the various modules are selected according to the problem to be solved, and a computer permits a control of the parameters for the various modules.

For each of these two examples a chromatographist can readily find the scheme of the connections required and the programming.

What is claimed is:

1. Chromatograph, more particularly for gas phase chromatography, comprising a modular enclosed space having compartments, temperature controlling means provided in each of said compartments, removable function modules selectively insertable in said compartments for providing selected different chromatography analysis functions, means provided in said compartments for receiving and releasably locking selected ones of said function modules, and means for selectively interconnecting said function modules according to the analysis problem to be solved.

2. Chromatograph according to claim 1, said modular enclosed space being defined by a housing forming a unitary structural assembly, said compartments being provided in said housing.

3. Chromatograph according to claim 1, comprising means for thermally insulating said compartments with respect to the surroundings and to each other.

4. Chromatograph according to claim 1, said temperature controlling means comprising heating means.

5. Chromatograph according to claim 1, said temperature controlling means comprising heating electrical resistances.

6. Chromatograph according to claim 1, said temperature controlling means comprising heating elements and a blower arranged in each compartment for providing a uniform temperature within said compartment.

7. Chromatograph according to claim 1, wherein said means for selectively interconnecting said function modules comprise an interchangeable connection matrix having external coupling positions, interconnecting means provided within said matrix for interconnecting said external coupling positions according to the analysis problem to be solved, coupling means provided on said function modules, and means for connecting said function module coupling means with said matrix external coupling positions when said function modules are arranged within said compartments.

8. Chromatograph according to claim 7, comprising means for automatically connecting said function module coupling means with said matrix external coupling positions when said function modules are arranged within said compartments.

9. Chromatograph according to claim 1, wherein said means for selectively interconnecting said function modules comprise a connection matrix having external coupling positions, movable interconnecting means provided within said matrix for interconnecting said external coupling positions, said interconnecting means being arrangeable according to the analysis problem to be solved, coupling means provided on said function modules, and means for connecting said function module coupling means with said matrix external coupling positions when said function modules are arranged within said compartments.

10. Chromatograph according to claim 9, comprising means for automatically connecting said function module coupling means with said matrix external coupling positions when said function modules are arranged within said compartments.

11. Chromatograph, more particularly for gas chromatography, comprising a modular enclosed space having compartments, temperature controlling means provided in each compartment, removable function modules selected from the group comprising injection modules, column modules, detection modules, valve modules, modules for physical conversion and modules for chemical conversion, selectively insertable in said compartments, means provided in said compartments for receiving and locking said function modules, and means for selectively interconnecting said function modules according to the analysis problem to be solved.

* * * * *